US012558944B2

(12) United States Patent
Kim et al.

(10) Patent No.: US 12,558,944 B2
(45) Date of Patent: Feb. 24, 2026

(54) VEHICLE AIR CONDITIONER HAVING PHOTOCATALYST MODULE

(71) Applicant: Hanon Systems, Daejeon (KR)

(72) Inventors: Jae Ho Kim, Daejeon (KR); Ji-Yong Park, Daejeon (KR); Tae Yong Park, Daejeon (KR); Su Jin Woo, Daejeon (KR); Sung Je Lee, Daejeon (KR)

(73) Assignee: HANON SYSTEMS, Daejeon (KR)

( * ) Notice: Subject to any disclaimer, the term of this patent is extended or adjusted under 35 U.S.C. 154(b) by 313 days.

(21) Appl. No.: 18/037,380

(22) PCT Filed: Dec. 28, 2021

(86) PCT No.: PCT/KR2021/020078
§ 371 (c)(1),
(2) Date: May 17, 2023

(87) PCT Pub. No.: WO2022/145987
PCT Pub. Date: Jul. 7, 2022

(65) Prior Publication Data
US 2023/0415548 A1 Dec. 28, 2023

(30) Foreign Application Priority Data

Dec. 29, 2020 (KR) ........................ 10-2020-0186171

(51) Int. Cl.
| | |
|---|---|
| *B60H 3/06* | (2006.01) |
| *A61L 9/18* | (2006.01) |
| *B01D 53/00* | (2006.01) |
| *B01D 53/88* | (2006.01) |
| *B60H 1/00* | (2006.01) |

(52) U.S. Cl.
CPC .............. *B60H 3/0608* (2013.01); *A61L 9/18* (2013.01); *B01D 53/007* (2013.01); *B01D 53/885* (2013.01); *B60H 1/00835* (2013.01); *A61L 2209/14* (2013.01); *B01D 2251/10* (2013.01); *B01D 2255/802* (2013.01);
(Continued)

(58) Field of Classification Search
CPC .......... B60H 2003/0675; B60H 3/0608; B60H 1/00521; B60H 1/00835; B01D 53/007; B01D 53/885; A61L 9/18
See application file for complete search history.

(56) References Cited

FOREIGN PATENT DOCUMENTS

| | | |
|---|---|---|
| CN | 201351231 | 4/2016 |
| CN | 209428324 | 9/2019 |

(Continued)

OTHER PUBLICATIONS

FR3062604 and translation (Year: 2018).*

(Continued)

*Primary Examiner* — Steven S Anderson, II
(74) *Attorney, Agent, or Firm* — NORTON ROSE FULBRIGHT US LLP

(57) ABSTRACT

The present invention relates to a vehicle air conditioner, and more particularly, to a vehicle air conditioner having a photocatalyst module, which provides an optimal design location or a mounting structure in which the photocatalyst module is mounted on an upper surface of a duct, the upper surface of the duct has a predetermined inclination with respect to a floor surface, and the photocatalyst module is mounted on a left/right independent air conditioner.

15 Claims, 7 Drawing Sheets

(52) U.S. Cl.
CPC ................ *B01D 2259/4566* (2013.01); *B01D 2259/804* (2013.01); *B60H 2003/0675* (2013.01)

(56)                   References Cited

FOREIGN PATENT DOCUMENTS

| | | | | |
|---|---|---|---|---|
| FR | 3062604 | A1 * | 8/2018 | ......... B60H 1/00849 |
| JP | H11245644 | A | 9/1999 | |
| JP | 2005024127 | | 1/2005 | |
| KR | 10-1446464 | B1 | 10/2014 | |
| KR | 2015-0125749 | A | 11/2015 | |
| KR | 20160036857 | | 4/2016 | |
| KR | 10-2016-0072765 | A | 6/2016 | |
| KR | 10-2014759 | B1 | 8/2019 | |
| KR | 10-2020-0137402 | A | 12/2020 | |
| WO | WO-2015111911 | A1 * | 7/2015 | ......... B60H 1/00521 |

OTHER PUBLICATIONS

WO2015111911 and translation (Year: 2015).*
English translation of Official Action issued Jun. 24, 2025 in related Chinese Patent Application No. 202180078089.1 , 22 pgs.

* cited by examiner

500

(a)                    (b)

<u>500</u>

(a)                    (b)

100          500

300

10

VEHICLE AIR CONDITIONER HAVING PHOTOCATALYST MODULE

CROSS REFERENCE TO RELATED APPLICATIONS

This application is a national phase under 35 U.S.C. § 371 of International Application No. PCT/KR2021/020078 filed on Dec. 28, 2021, which claims the benefit of priority from Korean Patent Application No. 10-2020-0186171 filed on Dec. 29, 2020. The entire contents of these applications are incorporated herein by reference in their entirety.

TECHNICAL FIELD

The present invention relates to a vehicle air conditioner, and more particularly, to a vehicle air conditioner having a photocatalyst module, which provides an optimal design location or a mounting structure in which the photocatalyst module is mounted on an upper surface of a duct, the upper surface of the duct has a predetermined inclination with respect to a floor surface, and the photocatalyst module is mounted on a left/right independent air conditioner.

BACKGROUND ART

A vehicle air conditioner refers to a device configured to heat or cool a vehicle interior by introducing outside air into the vehicle interior or circulating inside air in the vehicle interior to heat or cool the air. The vehicle air conditioner includes: a blower unit configured to introduce inside air or outside air and blow the air, and an air conditioning unit configured to condition the air blown from the blower unit and discharge the air into the vehicle interior.

There have been proposed various methods for providing comfort to a driver by purifying air before the air having passed through the air conditioner is discharged into the vehicle interior. Among the methods, as illustrated in FIG. 1, there is a method that purifies air by a photocatalyst module 4 provided in an air passageway of an air conditioner 3.

Meanwhile, recently, a so-called left/right independent air conditioner has been applied. The left/right independent air conditioner cools or heats a driver seat and a passenger seat separately by supplying flows of air with different temperatures to the driver seat and the passenger seat in the vehicle interior in response to the needs of occupants. A left/right independent air conditioner for a vehicle in the related art may have an air conditioning casing having an air passageway that allows an air inlet port and an air discharge port to communicate with each other, and a separation wall is provided to divide the air passageway into left and right air passageways. An air flow rate adjustment door may be installed forward of the separation wall and adjust a flow rate of air blown to the left and right air passageways of the air conditioning casing.

Even in the case of the above-mentioned left/right independent air conditioner, it is necessary to purify air by using the photocatalyst module. Because an inner flow path of the left/right independent air conditioner is divided into the left air passageway and the right air passageway, it is possible to consider a configuration in which a plurality of photocatalyst modules is provided in the air passageway. However, the configuration in which the plurality of photocatalyst modules is provided is restricted in consideration of a narrow mounting space for the photocatalyst module in the air conditioner, a relatively large amount of costs of the photocatalyst module, and the like. Therefore, there is a need for an optimal design location or structure capable of exhibiting maximum performance by using a minimum number of photocatalyst modules.

DOCUMENT OF RELATED ART (Patent Document 1) Korean Patent Application Laid-Open No. 2015-0125749 (Nov. 10, 2015)

DISCLOSURE

Technical Problem

The present invention has been made in an effort to solve the above-mentioned problems, and an object of the present invention is to provide an optimal design location or mounting structure for a photocatalyst module capable of exhibiting maximum performance by using a minimum number of photocatalyst modules.

Technical Solution

A vehicle air conditioner according to one aspect of the present invention includes: a duct configured to connect a blower unit, which introduces inside air and outside air, and an air conditioning unit, which exchanges heat with the introduced inside and outside air, so that the air flows between the blower unit and the air conditioning unit; and a photocatalyst module including a module casing, a body disposed at a lower side in the module casing and having a light source therein, and a carrier disposed below the body and configured to generate superoxide radicals by generating a photocatalytic reaction by using light emitted from the light source, in which the duct has a photocatalyst module mounting part having a hollow shape therein so that the carrier of the photocatalyst module passes through the photocatalyst module mounting part, and in which the photocatalyst module mounting part is provided on an upper outer wall of the duct.

The duct may have a fastening means disposed at the periphery of the photocatalyst module mounting part and configured to fasten the photocatalyst module onto the duct, and in which an upper surface of the fastening means is provided in parallel with a floor surface.

The module casing may have a tilting bracket provided at a position corresponding to the fastening means and having a fastening hole through which the tilting bracket is bound with the fastening means, and the tilting bracket may be provided in parallel with the floor surface.

The vehicle air conditioner may further include: an additional casing provided to surround at least a part of an upper surface of the photocatalyst module and configured to fix the photocatalyst module to the duct so that the photocatalyst module is in close contact with the duct, in which the additional casing has an additional bracket provided at a position corresponding to the fastening means and having a fastening hole through which the additional bracket is bound with the fastening means, in which the additional bracket is provided in parallel with the floor surface, and in which the additional bracket of the additional casing is bound with the fastening means to fix and mount the photocatalyst module to an upper surface of the duct.

The module casing may have a horizontal bracket provided in parallel with the body of the photocatalyst module, the additional casing may have an additional joint capable of being coupled to the horizontal bracket, and the additional joint may be coupled to the horizontal bracket at the same time when the additional bracket of the additional casing is bound with the fastening means.

The fastening means may have a hollow portion therein, and a screw thread may be formed on an inner peripheral surface of the hollow portion.

The fastening means may be provided in the form of a pipe having an upper surface parallel to the floor surface.

The fastening means may be respectively provided at left and right sides of the module mounting part, a left fastening means provided at the left side of the module mounting part may be disposed on a left outer wall of the duct, and a right fastening means provided at the right side of the module mounting part may be disposed on a right outer wall of the duct.

Any one of the left fastening means and the right fastening means may be disposed at a front side based on a forward/rearward direction of the module mounting part, and the other of the left fastening means and the right fastening means may be disposed at a rear side based on the forward/rearward direction of the module mounting part, such that the left fastening means and the right fastening means are disposed at different positions based on the forward/rearward direction of the module mounting part.

The module casing may have tilting brackets provided at positions corresponding to the left fastening means and the right fastening means and respectively bound with the left fastening means and the right fastening means, the tilting brackets may be respectively provided at the left and right sides of the module casing, and the tilting brackets may each be provided in parallel with the floor surface.

The vehicle air conditioner may further include: an additional casing provided to surround at least a part of an upper surface of the photocatalyst module and configured to fix the photocatalyst module to the duct so that the photocatalyst module is in close contact with the duct, in which the additional casing has additional brackets provided at positions corresponding to the left fastening means and the right fastening means and respectively bound with the left fastening means and the right fastening means, in which the additional brackets are respectively provided at the left and right sides of the module casing, in which the additional bracket are each provided in parallel with the floor surface, and in which the additional brackets of the additional casing are each bound with each of the fastening means to fix and mount the photocatalyst module to an upper surface of the duct.

The module casing may have horizontal brackets provided in parallel with the body of the photocatalyst module and respectively provided at the left and right sides of the module casing, the additional casing may have additional joints capable of being coupled to the horizontal brackets and respectively provided at the left and right sides of the additional casing, and the additional joints may each be coupled to each of the horizontal brackets at the same time when the additional brackets of the additional casing are each bound with each of the fastening means.

The left fastening means and the right fastening means may each have a hollow portion therein, and a screw thread may be formed on an inner peripheral surface of the hollow portion.

The left fastening means and the right fastening means may be integrated with the duct.

A separation wall may be provided in an air passageway in the air conditioning unit such that the air passageway in the air conditioning unit is divided into a left air passageway and a right air passageway, an air flow rate adjustment door may be provided forward of the separation wall and adjust a flow rate of air to be blown to the left air passageway and the right air passageway, and the photocatalyst module mounting part may be provided forward of the air flow rate adjustment door such that the photocatalyst module is positioned forward of the air flow rate adjustment door.

Advantageous Effects

According to the present invention, the tilting bracket of the photocatalyst module is provided in parallel with the floor surface, and the fastening means, which has the upper surface provided in parallel with the floor surface, is provided on the upper surface of the duct on which the photocatalyst module is mounted. Therefore, it is possible to easily fix and mount the photocatalyst module onto the duct and improve safety during the process.

Further, the general photocatalyst module, which is mass-produced in the related art, only needs to be changed to the module casing applied to the present invention, such that the mass production of the general photocatalyst module in the related art without manufacturing a new photocatalyst module.

Alternatively, the additional casing may be provided to the general photocatalyst module that is mass-produced in the related art. Therefore, it is possible to securely fix and mount the photocatalyst module to the upper surface of the duct without modifying the general photocatalyst module.

BEST MODE

Hereinafter, the present invention will be described with reference to the accompanying drawings.

Figure 1:
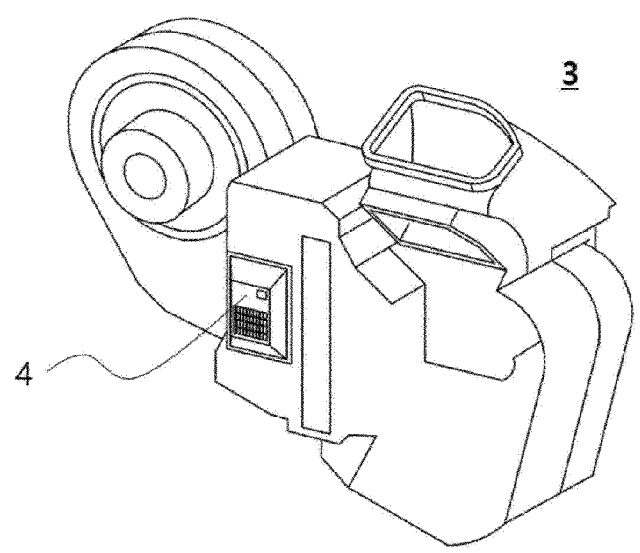
FIG. 1 is a view related to a vehicle air conditioner having a photocatalyst module in the related art.
Figure 2:
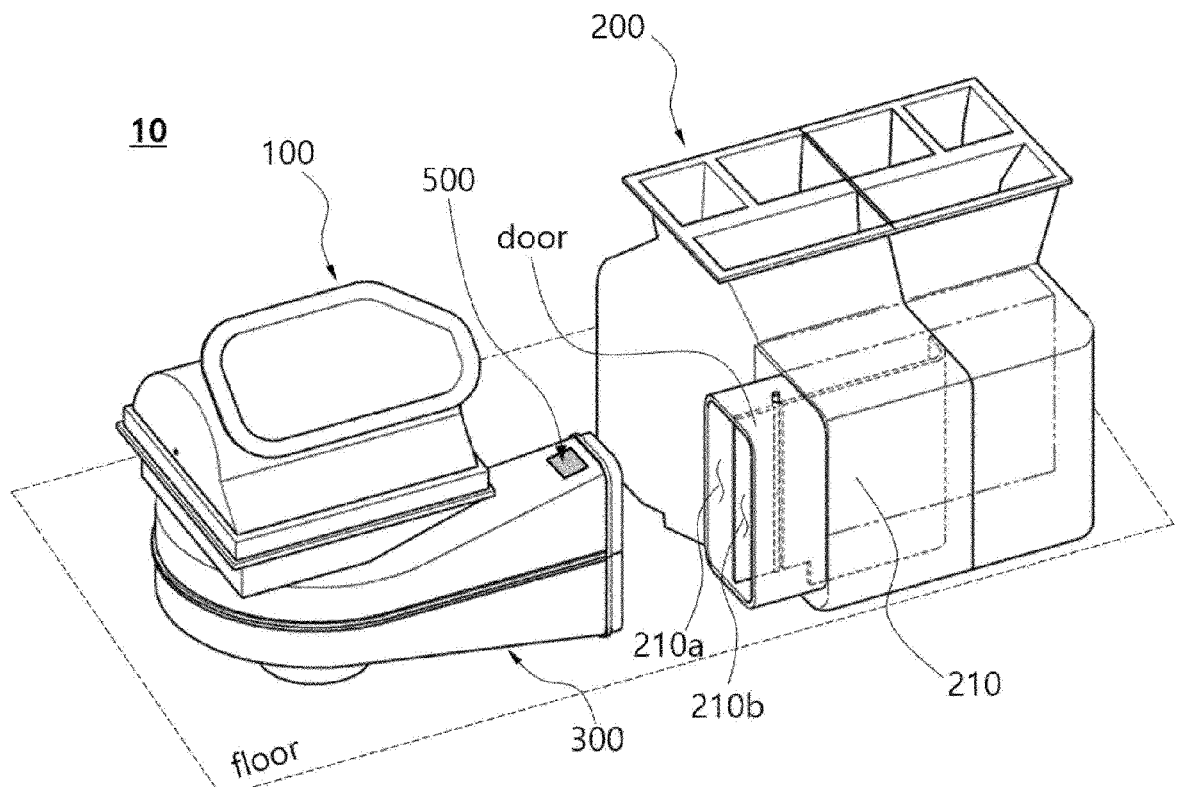
FIG. 2 is a view schematically illustrating a left/right independent air conditioner according to an embodiment of the present invention.

FIG. 2 is a view schematically illustrating a left/right independent air conditioner according to an embodiment of the present invention. An air conditioner 10 may include: a blower unit 100 configured to introduce inside air and outside air; an air conditioning unit 200 configured to exchange heat with the introduced inside and outside air; and a duct 300 configured to connect the blower unit and the air conditioning unit so that the air flows between the blower unit and the air conditioning unit.

An upper portion of the blower unit 100 may have an outside air inlet configured to provide a passageway through which outside air is sucked, and an inside air inlet configured to provide a passageway through which inside air is sucked. The inside air and the outside air, which are introduced into the blower unit, may flow to the air conditioning unit through the air passageway formed in the blower unit.

The air conditioning unit 200 serves to condition the inside and outside air introduced through the blower unit. An evaporator and a heater core may be disposed in an internal space of the air conditioning unit 200. A plurality of air discharge ports, such as a defrost vent, a floor vent, and a face vent may be formed in the internal space of the air conditioning unit 200. Doors may be coupled to the discharge ports, respectively. In the left/right independent air conditioner 10, the internal space of the air conditioning unit, which corresponds to a downstream side an overall air passageway may be divided into left and right air passageways 210a and 210b by a separation wall 210. An air flow rate adjustment door (door) may be installed forward of the separation wall 210 and adjust a flow rate of air to be blown to the left and right air passageways. In addition, an actuator for operating the air flow rate adjustment door may be mounted on a rotary shaft of the air flow rate adjustment door 220.

The duct 300 serves to connect the blower unit 100 and the air conditioning unit 200. An air passageway is formed in the duct 300, such that one side of the air passageway may communicate with the air passageway of the blower unit, and the other side of the air passageway may communicate with the air passageway in the air conditioning unit. The duct 300 may be integrated with the blower unit 100. In general, the duct 300 may be assembled and manufactured separately from the air conditioning unit 200 and then assembled and coupled to the air conditioning unit 200 so that the air passageway in the air conditioning unit 200 communicates with the air passageway in the duct 300. Alternatively, the air conditioner 10 may be manufactured as the duct 300 is assembled and coupled to the air conditioning unit 200 so that the air passageway in the air conditioning unit 200 communicates with the air passageway in the duct 300 integrated with the blower unit 100. In this case, the air flow rate adjustment door (door) may be installed at a point of a connection portion where the duct 300 and the air conditioning unit 200 are connected, and the point of the connection portion corresponds to an upstream side of the air passageway in the air conditioning unit 200, i.e., a front side of the separation wall 210.

Meanwhile, in general, the duct 300 of the air conditioner 10 has a structure in which a cross-sectional area of the air passageway therein increases as the distance from a downstream side (i.e., a side based on a direction from the blower unit 100 to the air conditioning unit 200) decreases in comparison with the upstream side. Therefore, as illustrated in FIG. 2, an upper surface of the duct may have a predetermined inclination with respect to a floor surface. In the present invention, the floor surface refers to a floor surface on which the air conditioner of the present invention. The floor surface may mean an imaginary surface parallel to a horizontal surface perpendicular to a direction in which the air conditioner stands when the air conditioner normally stands.

In the case of the left/right independent air conditioner having the above-mentioned structure, it is necessary to efficiently purify the air in the air conditioner by designing and disposing a photocatalyst module at an optimal position.

Figure 3:
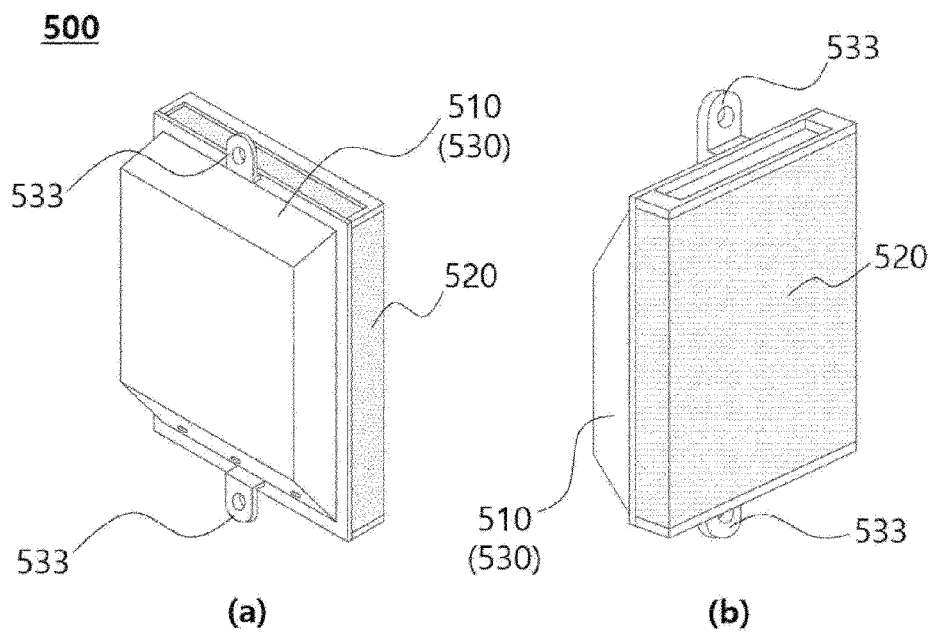
FIGS. 3A and 3B are front and rear perspective views of a photocatalyst module according to the embodiment of the present invention.
Figure 4:
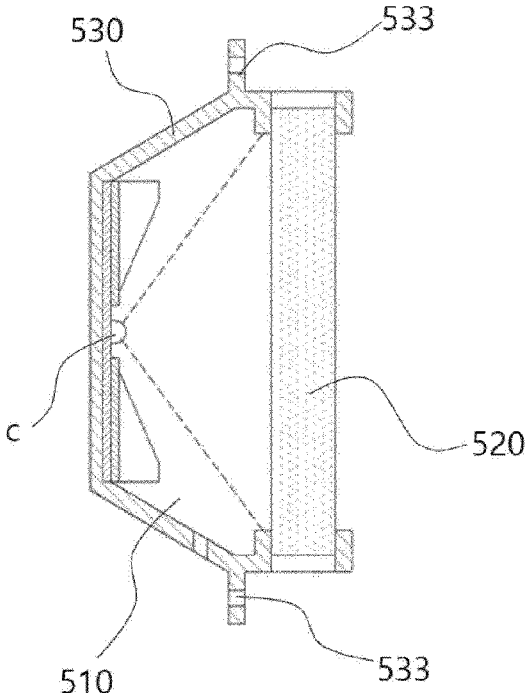
FIG. 4 is a transparent cross-sectional view of the photocatalyst module in FIG. 3.

Meanwhile, FIG. 3 illustrates a photocatalyst module 500 according to an embodiment of the present invention, in which FIG. 3A is a top perspective view of the photocatalyst module, and FIG. 3B is a bottom perspective view of the photocatalyst module. FIG. 4 is a transparent cross-sectional view of the photocatalyst module in FIG. 3. As illustrated, the photocatalyst module 500 according to the embodiment of the present invention may include: a body 510 having a light source c therein; and a carrier 520 disposed below the body and configured to generate superoxide radicals by generating a photocatalytic reaction by using light emitted from the light source. The photocatalyst module 500 may further include a module casing 530 that accommodates the body 510 and the carrier 520, such that the photocatalyst module 500 may be modularized into a single module. Therefore, the photocatalyst module may be easily installed in the air conditioner and conveniently attached or detached, which may be advantageous in performing maintenance.

Figure 5:
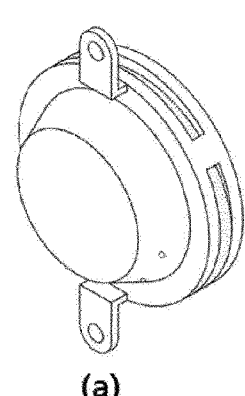
FIGS. 5A and 5B are front and rear perspective views of a photocatalyst module according to another embodiment of the present invention.
Figure 5:
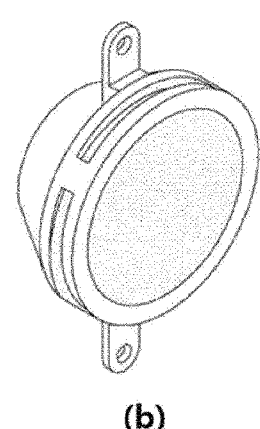

The carrier of the photocatalyst module may generate the superoxide radicals by generating the photocatalytic reaction by using the emitted light and be disposed to supply the generated superoxide radicals to the air flow path in the air conditioner. Contaminants introduced into the air conditioner, germs in an evaporator, various types of contaminants, and offensive odor may be removed by oxidation of the superoxide radicals generated by the photocatalyst module. More specifically, when the carrier absorbs ultraviolet rays emitted from the light source, electrons in a valence band filled with the electrons absorb light energy and jump to a conduction band that is not filled with the electrons. Positive holes, which are positions of the electrons in the valence band, oxidize water molecules on surfaces thereof and come into original states thereof, and the oxidized water molecules form OH radicals. In addition, excited electrons excited to the conduction band may react with oxygen and produce superoxide radicals with strong oxidizing power. As described above, in comparison with a structure that adsorbs and deodorizes contaminated air containing offensive odor, the photocatalyst module has the advantage of being able to be used almost semipermanently by selecting the type of carrier or performing appropriate On/Off control on the light source without changing a filter separately and the advantage of having excellent lifespan. Meanwhile, the photocatalyst module may have various shapes. As illustrated in FIG. 3, the photocatalyst module may have a quadrangular column shape as a whole. Alternatively, as illustrated in FIG. 5, the photocatalyst module may have a cylindrical shape.

Hereinafter, in the case of the air conditioner, which is the left/right independent air conditioner and has the structure in which the upper surface of the duct has a predetermined inclination with respect to the floor surface, an optimal design location and a mounting structure of the photocatalyst module will be described.

Figure 6:
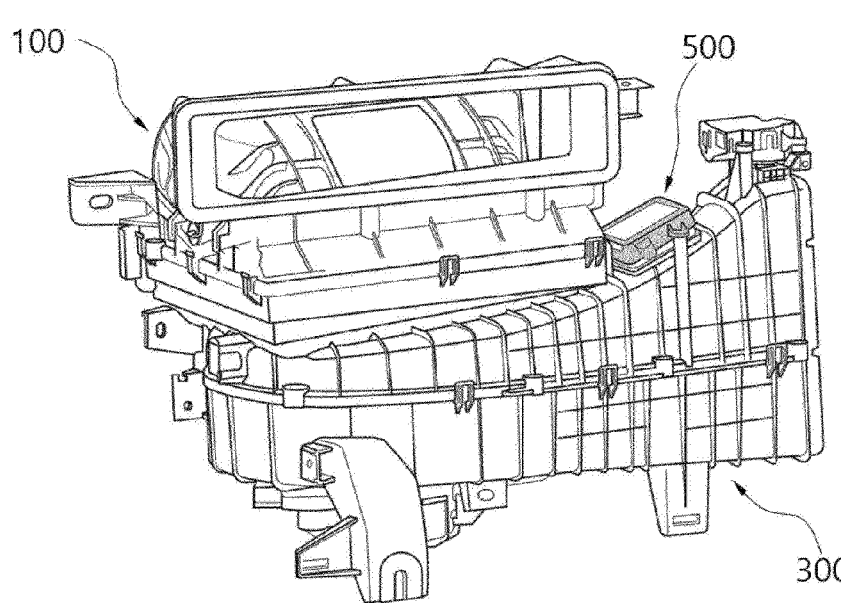
FIG. 6 is a view illustrating a photocatalyst module mounting structure according to the embodiment of the present invention.
Figure 7:
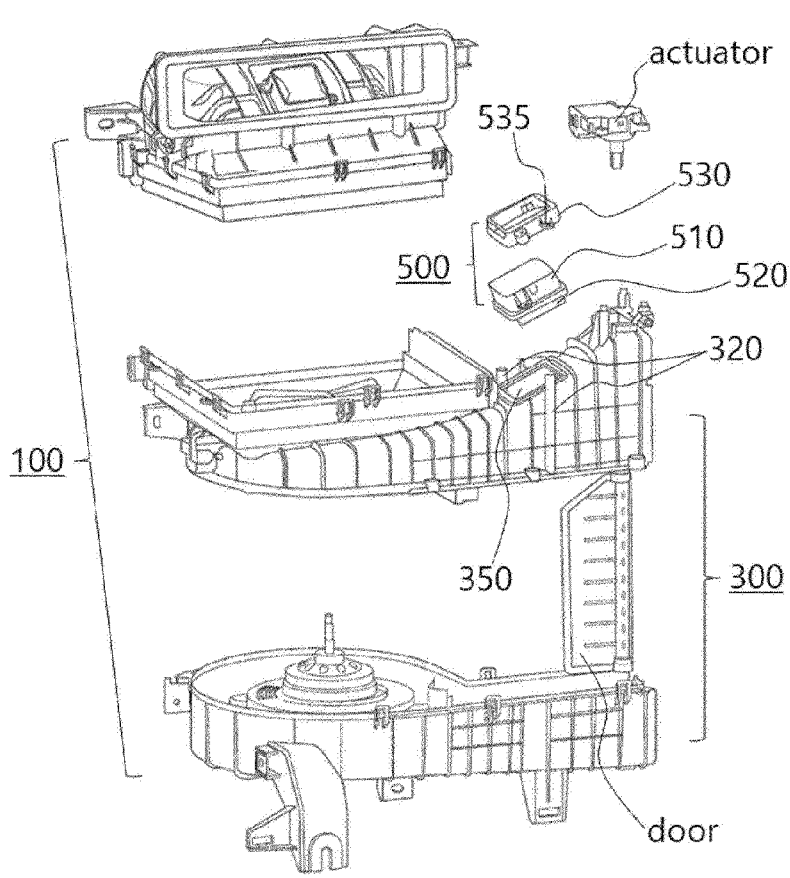
FIG. 7 is an exploded perspective view of FIG. 6.

FIG. 6 is a view illustrating a photocatalyst module mounting structure according to the embodiment of the present invention. More specifically, FIG. 6 illustrates that in the air conditioner in which the blower unit 100 and the duct 300 are integrated, the photocatalyst module 500 is mounted on an upper outer wall of the duct 300. FIG. 7 is an exploded perspective view in FIG. 6. As illustrated, the duct 300 may include a photocatalyst module mounting part 350 having a hollow shape therein so that the carrier 520 of the photocatalyst module 500 may pass through the photocatalyst module mounting part 350. The photocatalyst module mounting part 350 may be provided on the upper outer wall of the duct 300.

More specifically, the photocatalyst module mounting part 350 may include a mounting hole formed as a predetermined region of the upper outer wall of the duct has a hollow portion. Because the photocatalyst module is mounted on the photocatalyst module mounting part, the carrier may pass through an outer wall of the duct and protrude toward the inside of the duct, and the mounting hole may be closed by the body of the photocatalyst module. In addition, to fix the photocatalyst module in a state of being coupled to the outer wall of the duct as described above, the module casing 530 may have a bracket, and a fastening means may be further provided on the outer wall of the duct and disposed at a position corresponding to the bracket, such that the photocatalyst module may be securely fixed to the outer wall of the duct by bolting or the like between the bracket and the fastening means.

In this case, because the upper surface of the duct 300 has a predetermined angle with respect to the floor surface as described above, the photocatalyst module 500 mounted on the upper surface of the duct 300 may also have a predetermined angle with respect to the floor surface. In the above-mentioned situation, at the time of coupling the photocatalyst module and the duct by bolting, the coupling process cannot be performed in a direction perpendicular to the floor surface, i.e., in a vertically upward direction of the photocatalyst module, but the coupling process needs to be performed in a state inclined at a predetermined angle from a location vertically above the photocatalyst module in consideration of a degree to which the photocatalyst module is inclined, which causes a problem in that the coupling process is restricted by an intake duct of the blower unit, as illustrated. Further, a predetermined amount of force is applied to the duct to couple the duct by bolting. In case that the bolting is performed strongly, there is a risk that the duct is distorted or damaged at the time of performing the coupling process because the upper surface of the duct is inclined. When the bolting is performed loosely in consideration of the risk, there is a problem in that the photocatalyst module cannot be securely fixed. Hereinafter, specific contents of the present invention proposed to solve the above-mentioned problem will be described with reference to the specific embodiment.

Figure 8:
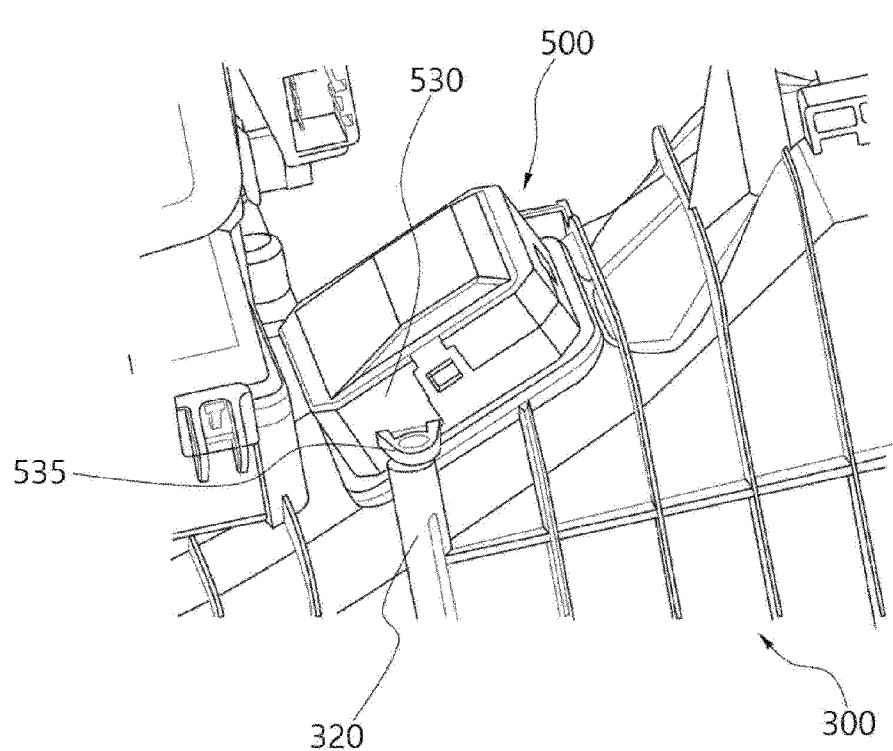
FIG. 8 is a view illustrating a photocatalyst module mounting structure according to a first example of the present invention.

Photocatalyst Module Mounting Structure
According to First Example of Present Invention FIG. 8 is an enlarged view of a photocatalyst module mounting structure according to a first example of the present invention. The duct 300 may have fastening means 320 provided at the periphery of the photocatalyst module mounting part 350. In this case, an upper surface of the fastening means 320 may be parallel to the floor surface. In addition, the module casing 530 may have tilting brackets 535 provided at positions corresponding to the fastening means 320 and each having a fastening hole through which the tilting bracket 535 is bound with the fastening means 320. In this case, the tilting bracket 535 is provided in parallel with the floor surface, such that a lower surface of the tilting bracket 535 is in close contact with an upper surface of the fastening means 320.

That is, in comparison with the general photocatalyst module in which a bracket 533 provided on the module casing 530 is provided in parallel with the body 510 of the photocatalyst module as described above with reference to FIGS. 3 and 5, the tilting bracket 535 of the module casing 530 of the photocatalyst module 500 of the present invention may be obliquely provided to have a predetermined angle with respect to the body 510 and thus be parallel to the floor surface instead of being parallel to the body 510 of the photocatalyst module. Further, the fastening means 320 may be provided on the duct and disposed at a position corresponding to the tilting bracket 535, and an upper surface of the fastening means 320 may be provided in parallel with the floor surface. Therefore, the tilting bracket 535 of the module casing of the photocatalyst module may be coupled to the fastening means 320 on the duct in the vertical direction by bolting. Therefore, an operator may perform the bolting process in the direction perpendicular to the floor surface, which not only facilitates the process but also solve a problem in that a visual field is blocked by the intake duct or the like when the tilting bracket of the module casing and the fastening means on the duct are viewed from vertically above. Therefore, the photocatalyst module may be fixedly mounted at an accurate position on the upper surface of the duct. Furthermore, because a force is applied from vertically above to vertically below during the bolting process, it is possible to remarkably reduce a risk that the duct is pushed or damaged during the process.

In addition, the general photocatalyst module (i.e., the photocatalyst module 500 in which the bracket 533 of the module casing 530 is parallel to the body), which is mass-produced in the related art, only needs to be changed to the module casing applied to the present invention, such that the mass production of the general photocatalyst module in the related art may be maintained without manufacturing a new photocatalyst module.

Figure 9:
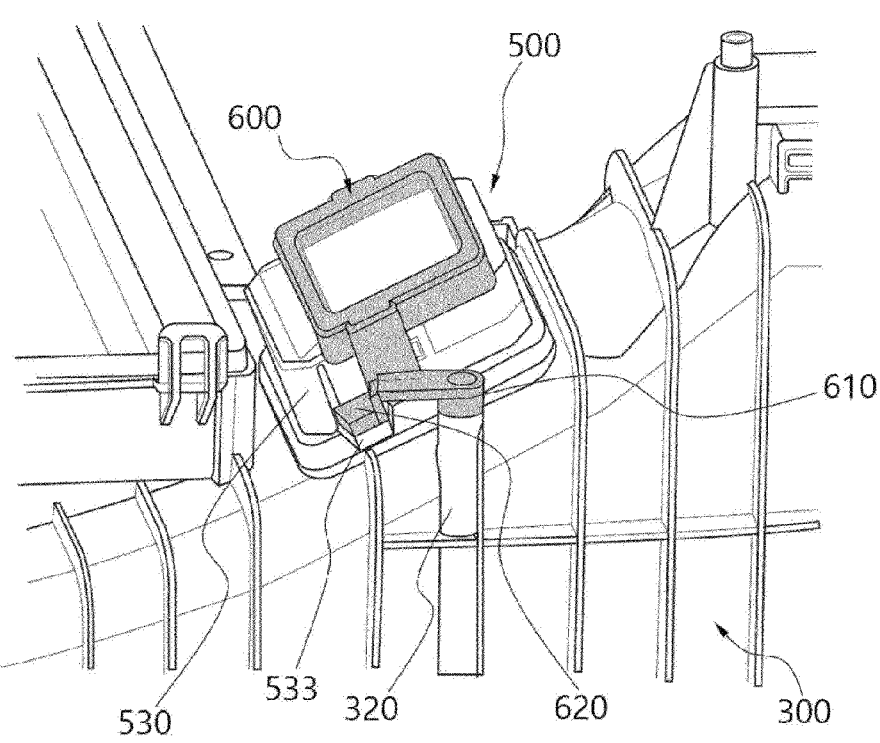
FIG. 9 is a view illustrating a photocatalyst module mounting structure according to a second example of the present invention.

Photocatalyst Module Mounting Structure
According to Second Example of Present Invention FIG. 9 is an enlarged view of a photocatalyst module mounting structure according to a second example of the present invention. Unlike the first example, the photocatalyst module of the second example may further include an additional casing 600, as illustrated. The additional casing 600 is provided to surround at least a part of an upper surface of the photocatalyst module 500 and serves to fix the photocatalyst module to the duct 300 so that the photocatalyst module is in close contact with the duct 300. The additional casing 600 may include additional brackets 610 provided at positions corresponding to the fastening means 320 and each having a fastening hole through which the additional bracket 610 is bound with the fastening means 320. In this case, like the above-mentioned tilting bracket 535 of the module casing 530, the additional bracket 610 may be provided in parallel with the floor surface. Because the additional casing is further provided as described above, the additional bracket of the additional casing may be bound with the fastening means, such that the photocatalyst module may be fixedly mounted on the upper surface of the duct.

That is, the additional casing 600 is a separate additional structure for coupling and fixing the photocatalyst module onto the duct. The additional casing surrounds a part of the upper surface of the photocatalyst module and is bound with the fastening means of the duct, such that the photocatalyst module may be securely fixed onto the duct. According to the second example of the present invention, as in the first example, the photocatalyst module may be securely fixed onto the duct without changing the module casing of the photocatalyst module in the related art. In this case, because the additional bracket of the additional casing is provided horizontally, the above-mentioned advantages, such as ease of the process and process safety, may be provided without change.

In this case, furthermore, in the case of the general photocatalyst module, i.e., the photocatalyst module having horizontal brackets 533 provided on the module casing 530 and disposed in parallel with the body of the photocatalyst module, the additional casing 600 may further include additional joints 620 capable of being coupled to the horizontal brackets 533, such that the photocatalyst module 500 may be fixed more stably. That is, as illustrated in FIG. 9, the additional casing 600 may further include the additional joint 620 capable of coupled to the horizontal bracket 533. The additional joint 620 of the additional casing is coupled to the horizontal bracket 533 of the photocatalyst module at the same time when the additional bracket 610 of the additional casing is bound with the fastening means 320, such that the photocatalyst module may be more securely fixedly mounted onto the duct. In this case, the additional joint and the horizontal bracket may be coupled in various ways. For example, the additional joint and the horizontal bracket may be fixedly coupled to each other as a pin formed on the additional joint is fitted with a mounting hole formed in the horizontal bracket.

Fastening Means According to One Example of Present Invention

Hereinafter, the fastening means according to the present invention will be specifically described with reference to FIGS. 6 to 9. The fastening means 320 may have a hollow portion therein, and a screw thread may be formed on an inner peripheral surface of the hollow portion, such that the fastening means 320 may be easily coupled, by bolting, to the tilting bracket 535 of the module casing 530 and/or the additional bracket 610 of the additional casing 600.

In this case, the fastening means may be provided in the form of a pipe. More specifically, the upper surface of the fastening means provided in the form of a pipe may be provided in parallel with the floor surface. As well illustrated in FIG. 7, an upper portion of the pipe may further protrude to a predetermined degree than the upper surface of the duct. The drawings illustrate that the pipe has a cylindrical shape. However, the pipe may have various shapes including a quadrangular column shape.

Figure 10:
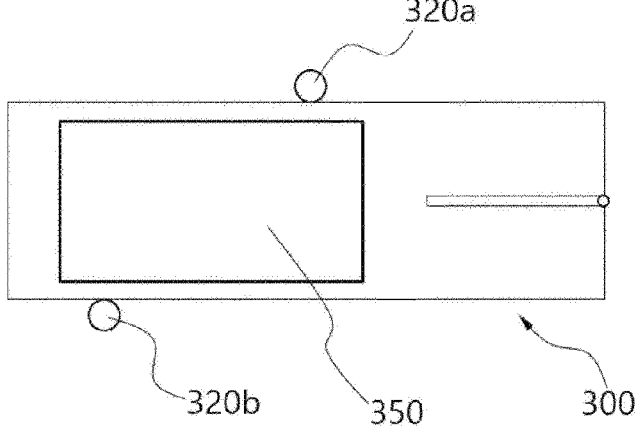
FIG. 10 is a conceptual view illustrating a duct in FIG. 6 when viewed from above.

In addition, the fastening means 320 may be provided as one or more fastening means. For example, the fastening means may be provided at left and right sides of the module mounting part. In this case, a left fastening means 320a may be disposed on a left outer wall of the duct 300, and a right fastening means 320b may be disposed on a right outer wall of the duct 300. FIG. 10 is a conceptual view when the duct in FIG. 6 is viewed from above. With reference to FIGS. 10 and 6, the fastening means 320a and 320b may be disposed to be perpendicular to lateral outer walls of the duct, which may increase an area in which the fastening means is in close contact with the duct in a longitudinal direction. Therefore, the fastening means 320a and 320b may more properly support the force applied from above to below during the bolting process. Meanwhile, separate fixing members for fixing the fastening means to the duct may be used to dispose the fastening means 320a and 320b on the lateral outer walls of the duct. However, it is more preferred that the fastening means are integrated with the duct. The duct and the fastening means may be integrally manufactured by including the fastening means in a mold for the duct.

Further, in case that the left fastening means 320a and the right fastening means 320b are provided, the left fastening means 320a and the right fastening means 320b may be disposed at different positions based on a forward/rearward direction of the module mounting part 350. That is, as illustrated in FIGS. 10 and 7, any one of the left fastening means 320a and the right fastening means 320b may be disposed at a front side based on the forward/rearward direction of the module mounting part, and the other of the left fastening means 320a and the right fastening means 320b may be disposed at a rear side based on the forward/rearward direction of the module mounting part. This configuration may be advantageous in dispersing the force applied at the time of mounting the photocatalyst module and may prevent the photocatalyst module from being distorted or rotated from an exact position by physical impact or the like after the photocatalyst module is mounted.

Meanwhile, as described above, the tilting bracket 535 of the module casing 530 and the additional bracket 610 of the additional casing 600 may be disposed to correspond to the position and structure of the fastening means 320 and respectively provided at the left side and the right side of the module casing 530 or at the left side and the right side of the additional bracket 600. In this case, the tilting bracket 535 of the module casing 530 and the additional bracket 610 of the additional casing 600 may be, of course, provided in parallel with the floor surface. The description of the specific contents will be substituted with the above-mentioned description of the photocatalyst module mounting structures according to the first and second examples.

Figure 11:
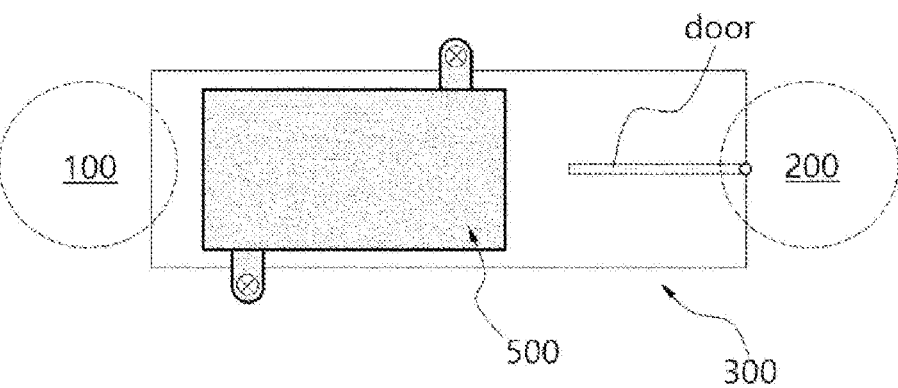
FIG. 11 is a conceptual view illustrating a vehicle air conditioner in FIG. 6 when viewed from above.

Meanwhile, as described above, in the left/right independent air conditioner 10, the air flow rate adjustment door (door) may be installed at the point of the connection portion where the duct 300 and the air conditioning unit 200 are connected, and the point of the connection portion corresponds to the upstream side of the air passageway in the air conditioning unit 200, i.e., the front side of the separation wall 210. With reference back to FIG. 2, the left/right independent air conditioner may have the separation wall 210 provided in the air passageway in the air conditioning unit 200, such that the air passageway in the air conditioning unit may be divided into the left air passageway 210a and the right air passageway 210b. The air flow rate adjustment door (door) may be provided forward of the separation wall 210 and adjust a flow rate of air to be blown to the left air passageway 210a and the right air passageway 210b. In the above-mentioned left/right independent air conditioner according to the present invention, the photocatalyst module mounting part 350 may be provided forward of the air flow rate adjustment door (door), such that the photocatalyst module 500 may be provided forward of the air flow rate adjustment door (door). That is, FIG. 11 is a conceptual view illustrating the vehicle air conditioner in FIG. 6 when viewed from above. As illustrated, the photocatalyst module 500 may be disposed on the duct 300 and provided forward of the air flow rate adjustment door 200 and purify the air before the air introduced through the blower unit 100 is separated and flows into the left and right air passageways 210a and 210b of the air conditioning unit 200. Therefore, it is possible to expect sufficient purification and sterilization effects by using the single photocatalyst module.

As described above, the vehicle air conditioner according to the present invention is the left/right independent air conditioner, i.e., the air conditioner having the structure in which the upper surface of the duct has a predetermined inclination with respect to the floor surface. Therefore, it is possible to provide the optimal design location or the mounting structure capable of purifying air by using a minimum number of photocatalyst modules and easily and securely mounting the photocatalyst module.

While the embodiments of the present invention have been described with reference to the accompanying drawings, those skilled in the art will understand that the present invention may be carried out in any other specific form without changing the technical spirit or an essential feature thereof. Therefore, it should be understood that the above-described embodiments are illustrative in all aspects and do not limit the present invention.

DESCRIPTION OF REFERENCE NUMERALS

10: Vehicle air conditioner 100: Blower unit
200: Air conditioning unit
210: Separation wall
210a, 210b: Left air passageway, Right air passageway
300: Duct
320: Fastening means
320a, 320b: Left fastening means, Right fastening means
350: Photocatalyst module mounting part
500: Photocatalyst module
510: Body
520: Carrier
530: Module casing
533: Horizontal bracket
535: Tilting bracket
600: Additional casing
610: Additional bracket
620: Additional joint
door: Air flow rate adjustment door

The invention claimed is:

1. A vehicle air conditioner comprising:
a duct configured to connect a blower unit, which introduces inside air and outside air, and an air conditioning unit, which exchanges heat with the introduced inside and outside air, so that the air flows between the blower unit and the air conditioning unit; and
a photocatalyst module comprising a module casing, a body disposed at a lower side in the module casing and having a light source therein, and a carrier disposed below the body and configured to generate superoxide radicals by generating a photocatalytic reaction by using light emitted from the light source,
wherein the duct has a photocatalyst module mounting part having a hollow shape therein so that the carrier of the photocatalyst module passes through the photocatalyst module mounting part,
wherein the photocatalyst module mounting part is provided on an upper outer wall of the duct,
wherein the duct has a fastener disposed at the periphery of the photocatalyst module mounting part and configured to fasten the photocatalyst module onto the duct,
wherein an upper surface of the fastener is provided in parallel with a floor surface,
wherein the module casing has a tilting bracket provided at a position corresponding to the fastener and having a fastening hole through which the tilting bracket is bound with the fastener,
wherein the tilting bracket is provided in parallel with the floor surface,
wherein the tilting bracket is obliquely provided to have a predetermined angle with respect to the body and thus be parallel to the floor surface, and wherein the floor surface references a surface parallel to a horizontal surface perpendicular to a direction in which the vehicle air conditioner stands when the vehicle air conditioner stands.

2. The vehicle air conditioner of claim 1, further comprising:
an additional casing provided to surround at least a part of an upper surface of the photocatalyst module and configured to fix the photocatalyst module to the duct so that the photocatalyst module is in contact with the duct,
wherein the additional casing has an additional bracket provided at a position corresponding to the fastener and having a fastening hole through which the additional bracket is bound with the fastener,
wherein the additional bracket is provided in parallel with the floor surface, and
wherein the additional bracket of the additional casing is bound with the fastener to fix and mount the photocatalyst module to an upper surface of the duct.

3. The vehicle air conditioner of claim 2, wherein the module casing has a horizontal bracket provided in parallel with the body of the photocatalyst module,
wherein the additional casing has an additional joint capable of being coupled to the horizontal bracket, and
wherein the additional joint is coupled to the horizontal bracket at the same time when the additional bracket of the additional casing is bound with the fastener.

4. The vehicle air conditioner of claim 1, wherein the fastener has a hollow portion therein, and a screw thread is formed on an inner peripheral surface of the hollow portion.

5. The vehicle air conditioner of claim 1, wherein the fastener is provided in the form of a pipe having an upper surface parallel to the floor surface.

6. The vehicle air conditioner of claim 5, comprising two fasteners, wherein the fasteners are respectively provided at left and right sides of the module mounting part,
wherein a left fastener provided at the left side of the module mounting part is disposed on a left outer wall of the duct, and
wherein a right fastener provided at the right side of the module mounting part is disposed on a right outer wall of the duct.

7. The vehicle air conditioner of claim 6, wherein any one of the left fastener and the right fastener is disposed at a front side based on a forward/rearward direction of the module mounting part, and the other of the left fastener and the right fastener is disposed at a rear side based on the forward/rearward direction of the module mounting part, such that the left fastener and the right fastener are disposed at different positions based on the forward/rearward direction of the module mounting part.

8. The vehicle air conditioner of claim 6, wherein the module casing has tilting brackets provided at positions corresponding to the left fastener and the right fastener and respectively bound with the left fastener and the right fastener,
wherein the tilting brackets are respectively provided at the left and right sides of the module casing, and
wherein the tilting brackets are each provided in parallel with the floor surface.

9. The vehicle air conditioner of claim 6, further comprising:
an additional casing provided to surround at least a part of an upper surface of the photocatalyst module and configured to fix the photocatalyst module to the duct so that the photocatalyst module is in contact with the duct, wherein the additional casing has additional brackets provided at positions corresponding to the left fastener and the right fastener and respectively bound with the left fastener and the right fastener, wherein the additional brackets are respectively provided at the left and right sides of the module casing, wherein the additional bracket are each provided in parallel with the floor surface, and wherein the additional brackets of the additional casing are each bound with each of the fasteners to fix and mount the photocatalyst module to an upper surface of the duct.

10. The vehicle air conditioner of claim 9, wherein the module casing has horizontal brackets provided in parallel with the body of the photocatalyst module and respectively provided at the left and right sides of the module casing, wherein the additional casing has additional joints capable of being coupled to the horizontal brackets and respectively provided at the left and right sides of the additional casing, and wherein the additional joints are each coupled to each of the horizontal brackets at the same time when the additional brackets of the additional casing are each bound with each of the fasteners.

11. The vehicle air conditioner of claim 6, wherein the left fastener and the right fastener each have a hollow portion therein, and a screw thread is formed on an inner peripheral surface of the hollow portion.

12. The vehicle air conditioner of claim 6, wherein the left fastener and the right fastener are integrated with the duct.

13. The vehicle air conditioner of claim 1, wherein a separation wall is provided in an air passageway in the air conditioning unit, such that the air passageway in the air conditioning unit is divided into a left air passageway and a right air passageway, wherein an air flow rate adjustment door is provided upstream of the separation wall and adjusts a flow rate of air to be blown to the left air passageway and the right air passageway, and wherein the photocatalyst module mounting part is provided upstream of the air flow rate adjustment door, such that the photocatalyst module is positioned upstream of the air flow rate adjustment door.

14. A vehicle air conditioner comprising:

a duct configured to connect a blower unit, which introduces inside air and outside air, and an air conditioning unit, which exchanges heat with the introduced inside and outside air, so that the air flows between the blower unit and the air conditioning unit; and a photocatalyst module comprising a module casing, a body disposed at a lower side in the module casing and having a light source therein, and a carrier disposed below the body and configured to generate superoxide radicals by generating a photocatalytic reaction by using light emitted from the light source, an additional casing provided to surround at least a part of an upper surface of the photocatalyst module and configured to fix the photocatalyst module to the duct so that the photocatalyst module is in contact with the duct, wherein the duct has a photocatalyst module mounting part having a hollow shape therein so that the carrier of the photocatalyst module passes through the photocatalyst module mounting part, wherein the photocatalyst module mounting part is provided on an upper outer wall of the duct, wherein the duct has a fastener disposed at the periphery of the photocatalyst module mounting part and configured to fasten the photocatalyst module onto the duct, wherein an upper surface of the fastener is provided in parallel with a floor surface, wherein the additional casing has an additional bracket provided at a position corresponding to the fastener and having a fastening hole through which the additional bracket is bound with the fastener, wherein the additional bracket is provided in parallel with the floor surface, wherein the additional bracket of the additional casing is bound with the fastener to fix and mount the photocatalyst module to an upper surface of the duct, wherein the module casing has a horizontal bracket provided in parallel with the body of the photocatalyst module, wherein the additional casing has an additional joint capable of being coupled to the horizontal bracket, and wherein the additional joint is coupled to the horizontal bracket at the same time when the additional bracket of the additional casing is bound with the fastener.

15. A vehicle air conditioner comprising:

a duct configured to connect a blower unit, which introduces inside air and outside air, and an air conditioning unit, which exchanges heat with the introduced inside and outside air, so that the air flows between the blower unit and the air conditioning unit; and a photocatalyst module comprising a module casing, a body disposed at a lower side in the module casing and having a light source therein, and a carrier disposed below the body and configured to generate superoxide radicals by generating a photocatalytic reaction by using light emitted from the light source, wherein the duct has a photocatalyst module mounting part having a hollow shape therein so that the carrier of the photocatalyst module passes through the photocatalyst module mounting part, wherein the photocatalyst module mounting part is provided on an upper outer wall of the duct, wherein the duct has a fastener disposed at the periphery of the photocatalyst module mounting part and configured to fasten the photocatalyst module onto the duct, wherein an upper surface of the fastener is provided in parallel with a floor surface, and wherein the fastener is provided in the form of a pipe having an upper surface parallel to the floor surface.

* * * * *